(12) United States Patent
Shikata (10) Patent No.: US 11,364,521 B2
(45) Date of Patent: Jun. 21, 2022

(54) ULTRASONIC TRANSDUCER AND ULTRASONIC PROBE

(71) Applicant: CANON MEDICAL SYSTEMS CORPORATION, Otawara (JP)

(72) Inventor: Hiroyuki Shikata, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 752 days.

(21) Appl. No.: 15/906,541

(22) Filed: Feb. 27, 2018

(65) Prior Publication Data

US 2018/0250711 A1    Sep. 6, 2018

(30) Foreign Application Priority Data

Mar. 3, 2017  (JP) .............................. JP2017-040737

(51) Int. Cl.
*B06B 1/06*    (2006.01)
*A61B 8/00*    (2006.01)
*B06B 1/02*    (2006.01)

(52) U.S. Cl.
CPC .......... *B06B 1/0622* (2013.01); *A61B 8/4444* (2013.01); *A61B 8/4494* (2013.01); *B06B 1/0215* (2013.01); *B06B 2201/76* (2013.01)

(58) Field of Classification Search
CPC combination set(s) only.
See application file for complete search history.

(56) References Cited

U.S. PATENT DOCUMENTS

| 6,503,204 B1* | 1/2003 | Sumanaweera ....... B06B 1/0622 |
| | | 600/459 |
| 2009/0001853 A1 | 1/2009 | Adachi et al. |

(Continued)

FOREIGN PATENT DOCUMENTS

| JP | 2007-229328 | 9/2007 |
| JP | 2013-62571 A | 4/2013 |

(Continued)

OTHER PUBLICATIONS

Japanese Office Action dated Oct. 27, 2020 in Japanese Patent Application No. 2017-040737, 3 pages.

*Primary Examiner* — Bryan P Gordon
(74) *Attorney, Agent, or Firm* — Oblon, McClelland, Maier & Neustadt, L.L.P.

(57) ABSTRACT

An ultrasonic transducer according to an embodiment includes a piezoelectric layer, a first electrode, a second electrode, a base layer, and a substrate. The first electrode is disposed in a front side of the piezoelectric layer and extends along a first direction. The second electrode is disposed in a back side of the piezoelectric layer and extends along a second direction intersecting with the first direction. The base layer is disposed in a back side of the second electrode. The substrate is disposed in a back side of the base layer. Each of the first electrode and the second electrode includes an overlap portion where the first electrode and the second electrode overlap each other when viewed from the front side of the piezoelectric layer. The substrate is provided with a cavity on a back side of the overlap portion on each of the first electrode and the second electrode. Each of the first electrode and the second electrode has the width of the overlap portion that is larger than the width of a peripheral portion of the overlap portion.

16 Claims, 8 Drawing Sheets

(56) References Cited

U.S. PATENT DOCUMENTS

| | | | |
|---|---|---|---|
| 2010/0201222 A1 | 8/2010 | Adachi et al. | |
| 2010/0327695 A1* | 12/2010 | Goel | B06B 1/0611 |
| | | | 310/320 |
| 2012/0256519 A1* | 10/2012 | Tomiyoshi | B81C 1/00626 |
| | | | 310/300 |
| 2013/0123629 A1* | 5/2013 | Rosenberg | A61B 8/429 |
| | | | 600/442 |
| 2016/0089111 A1* | 3/2016 | Yamada | B06B 1/0629 |
| | | | 600/459 |
| 2017/0170383 A1* | 6/2017 | Sammoura | B06B 1/0622 |
| 2018/0250711 A1* | 9/2018 | Shikata | B06B 1/0622 |

FOREIGN PATENT DOCUMENTS

| | | |
|---|---|---|
| JP | 2013-179404 A | 9/2013 |
| JP | 2014-127921 | 7/2014 |

\* cited by examiner

ULTRASONIC TRANSDUCER AND ULTRASONIC PROBE

CROSS-REFERENCE TO RELATED APPLICATIONS

This application is based upon and claims the benefit of priority from Japanese Patent Application No. 2017-040737, filed on Mar. 3, 2017; the entire contents of which are incorporated herein by reference.

FIELD

Embodiments described herein relate generally to an ultrasonic transducer and an ultrasonic probe.

BACKGROUND

A piezoelectric micromachined ultrasound transducer (pMUT) is one of ultrasonic transducers of an ultrasonic diagnostic device. For example, a pMUT has a bimorph structure in which a monocrystalline silicon thin film and a piezoelectric thin film with electrodes disposed on both sides are laminated. Expansion and contraction of the piezoelectric thin film causes an ultrasound wave to be received and transmitted. A pMUT generally has a plurality of transducer elements aligned and driven in parallel.

Capacitance is generated in a portion where the transducer elements are coupled with each other; however, because no cavities are provided to the portion, the capacitance makes no contributions to the transmission and receipt of an ultrasound wave, thereby decreasing efficiency in transmitting and receiving an ultrasound wave.

Moreover, piezoelectricity on an edge portion of the cavity formed on a substrate interrupts free vibration of the transducer constituted by films, which may degrade frequency response. The piezoelectricity may further cause deterioration of the edge portion of the cavity.

DETAILED DESCRIPTION

An ultrasonic transducer according to an embodiment includes a piezoelectric layer, a first electrode, a second electrode, a base layer, and a substrate. The first electrode is disposed in a front side of the piezoelectric layer and extends along a first direction. The second electrode is disposed in a back side of the piezoelectric layer and extends along a second direction intersecting with the first direction. The base layer is disposed in a back side of the second electrode. The substrate is disposed in a back side of the base layer. Each of the first electrode and the second electrode includes an overlap portion where the first electrode and the second electrode overlap each other when viewed from the front side of the piezoelectric layer. The substrate has a cavity formed on a back side of the overlap portion of the first electrode and the second electrode. Each of the first electrode and the second electrode has the width of the overlap portion that is larger than the width of a peripheral portion of the overlap portion.

Embodiments will now be described with reference to the drawings.

Embodiments

Figure 1:
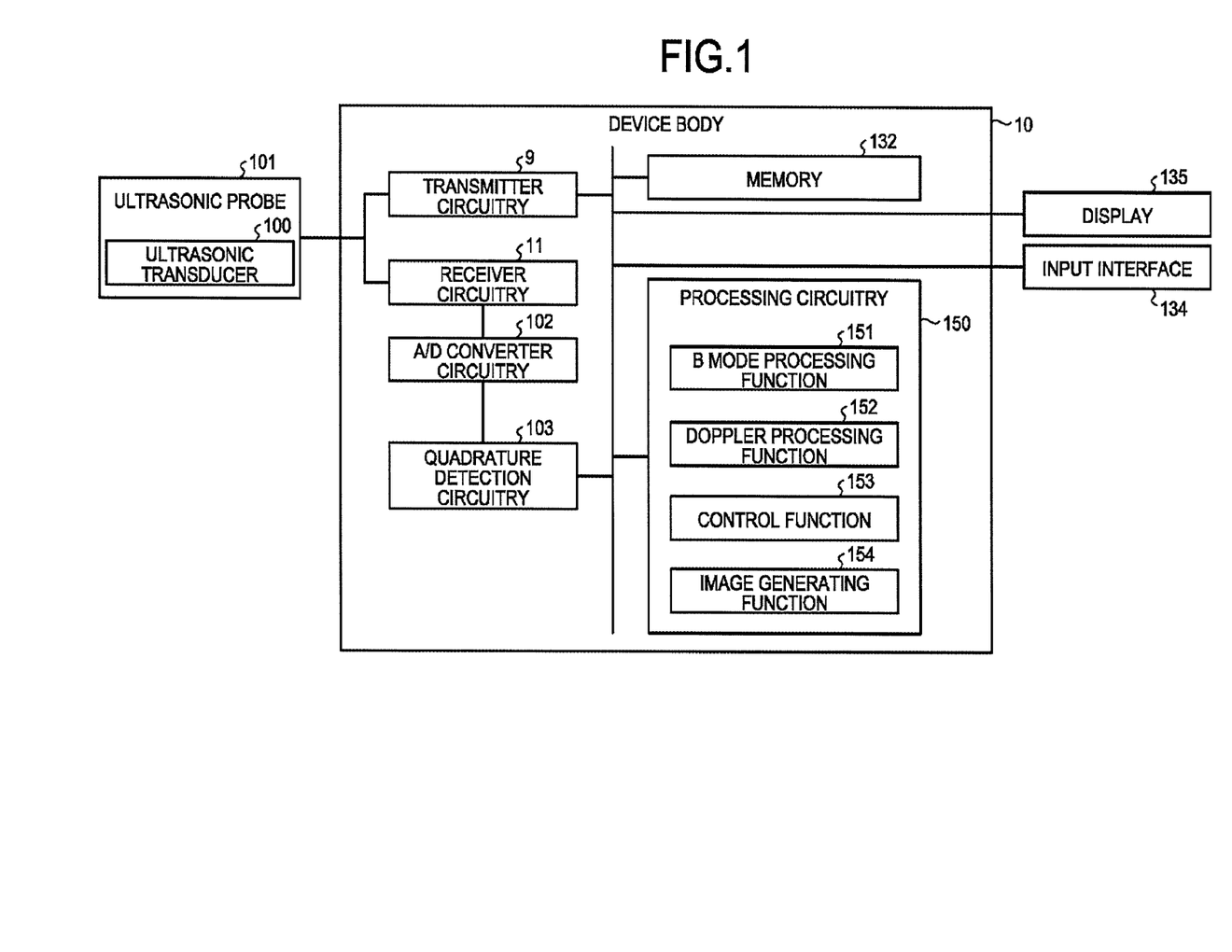
FIG. 1 is a drawing that illustrates an exemplary ultrasonic diagnostic device to which an ultrasonic probe according to an embodiment is installed.

A construction of an ultrasonic diagnostic device to which the ultrasonic probe according to the embodiment is installed will now be described. FIG. 1 is a drawing that illustrates an exemplary construction of the ultrasonic diagnostic device to which the ultrasonic probe according to the embodiment is installed. As illustrated in FIG. 1, the ultrasonic diagnostic device according to the embodiment includes an ultrasonic probe 101, a device body 10, a display 135, and input interface 134.

The ultrasonic probe 101 has a plurality of ultrasonic transducers (transducers) 100. The ultrasonic transducers 100 generate an ultrasound wave based on a driving signal supplied from transmitter circuitry 9 included in the later-described device body 10. The ultrasonic transducers 100 included in the ultrasonic probe 101 receive a reflected wave from a subject P and convert the reflected wave to an electric signal (a reflected wave signal). The ultrasonic probe 101 has a matching layer that is provided to the ultrasonic transducer 100, a backing member that prevents propagation of an ultrasound wave in a backward direction from a piezoelectric transducer element, and so on. The ultrasonic probe 101 is removably connected with the device body 10. A single ultrasonic transducer 100 may constitute a channel of the ultrasonic probe 101, or a plurality of ultrasonic transducers 100 may together constitute a channel of the ultrasonic probe 101.

When an ultrasound wave is transmitted from the ultrasonic probe 101 to the subject P, the transmitted ultrasound wave is subsequently reflected on discontinuous surfaces of acoustic impedance in the body tissues of the subject P, received by the ultrasonic transducers 100 of the ultrasonic probe 101 as a reflected wave, and converted to a reflected wave signal. The amplitude of the reflected wave signal depends on a difference in acoustic impedance on the discontinuous surface on which the ultrasound wave is reflected. When a transmitted ultrasonic pulse is reflected on a surface of a moving body such as a blood flow and a heart wall, the reflected wave signal depends on the velocity components of the moving body with respect to a direction in which the ultrasound wave is transmitted and is therefore subjected to frequency shift because of the Doppler effect.

Figure 2:
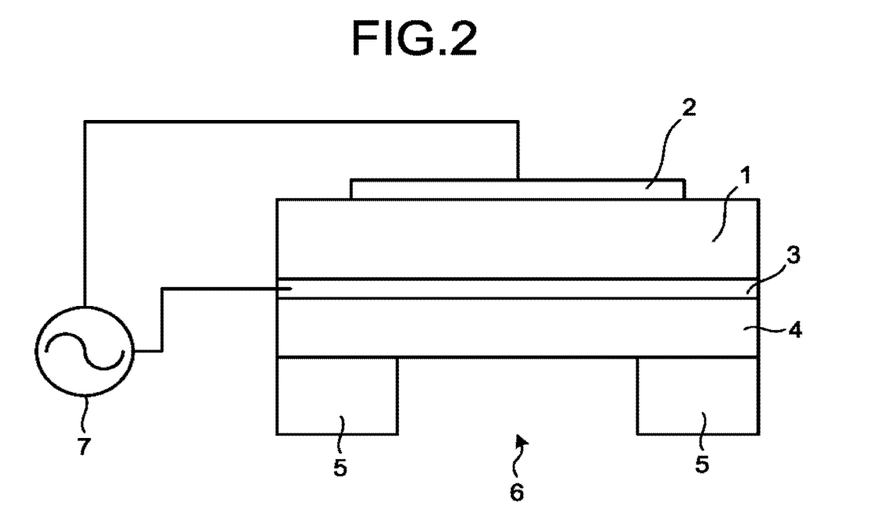
FIG. 2 is a drawing that illustrates an exemplary construction of an ultrasonic transducer according to the embodiment.

An exemplary construction of the ultrasonic transducer 100 is illustrated in FIG. 2 in a sectional surface. FIG. 2 is a drawing that illustrates an exemplary construction of the ultrasonic transducer 100 according to the embodiment. The ultrasonic transducer 100 includes a piezoelectric layer 1, a first electrode 2, a second electrode 3, a base layer 4, and a substrate 5. A power supply 7 and wiring portions arranged from the power supply 7 to the first electrode 2 and the second electrode 3 are not included in the ultrasonic transducer 100.

The piezoelectric layer 1 is a thin film including a piezoelectric body. The piezoelectric layer 1 produces a piezoelectric effect that is a phenomenon causing polarization in proportion to pressure applied to a substance and an inverse piezoelectric effect.

The first electrode 2 is an electrode positioned in the front side of the piezoelectric layer 1. The "front side" is a side closer to the subject P, that is, a side closer to the matching layer. The first electrode 2 is constituted of a conductive substance. When the ultrasonic transducer 100 transmits an ultrasound wave, the first electrode 2 is connected to the alternating-current power supply 7 of transmitter circuitry 9. When the ultrasonic transducer 100 receives an ultrasound wave, the first electrode 2 is connected to receiver circuitry 11. Arrangement of the first electrode 2 on the piezoelectric layer 1 will be described later in detail.

The second electrode 3 is an electrode positioned in a back side of the piezoelectric layer 1. The "back side" is a side away from the subject P, that is, for example, a side with the backing member. The second electrode 3 is constituted of a conductive substance. When the ultrasonic transducer 100 transmits an ultrasound wave, the second electrode 3 is connected to the alternating-current power supply 7 of the transmitter circuitry 9. When the ultrasonic transducer 100 receives an ultrasound wave, the second electrode 3 is connected to the receiver circuitry 11. Arrangement of the second electrode 3 on the piezoelectric layer 1 will also be described later in detail.

The base layer 4 is a layer forming a bimorph structure along with the piezoelectric layer 1 having electrodes on both surfaces. The base layer 4 is formed in the back side of the second electrode 3. The base layer 4 is made of, for example, a monocrystalline silicon thin film.

The substrate 5 is formed in the back side of the base layer 4. The substrate 5 is made of, for example, a silicon series member.

The substrate 5 is provided with cavities 6 so as to vibrate the base layer 4 and the piezoelectric layer 1. The cavity 6 is generally in a column shape including, for example, a cylindrical shape as illustrated in FIG. 2. In this embodiment, however, the shape is not limited thereto. The cavity 6 may be in another shape such as a circular truncated cone shape. If the cavity 6 is in a circular truncated cone shape, the diameter of a portion of the cavity 6 contacting the base layer 4 will be referred to as a "diameter of the cavity 6".

Because the base layer 4 is fixed to the substrate 5 in a place with no cavities 6 formed, neither the base layer 4 nor the piezoelectric layer 1 vibrates in this place. In a place where the cavity 6 is formed, the base layer 4 is not fixed to the substrate 5 and is free to be displaced. The base layer 4 and the piezoelectric layer 1 therefore easily vibrate in this place. In this manner, the formation of the cavity 6 allows the base layer 4 and the piezoelectric layer 1 to easily vibrate.

Based on this construction, operation when the alternating-current power supply 7 is applied to the ultrasonic transducer 100 will now be described. When a voltage is applied to both ends of the piezoelectric layer 1, the piezoelectric layer 1 is displaced due to the inverse piezoelectric effect. More specifically, when an alternating voltage is applied to both ends of the piezoelectric layer 1, the piezoelectric layer 1 vibrates due to the inverse piezoelectric effect. The vibration of the piezoelectric layer 1 is transmitted to the base layer 4, and the piezoelectric layer 1 and the base layer 4 particularly vibrate heavily immediately above an area with the cavity 6 formed. This vibration is transmitted as an ultrasound wave. In this manner, an electric signal is converted to mechanical displacement.

Operation when the ultrasonic transducer 100 detects vibration will now be described. As described above, the piezoelectric layer 1 and the base layer 4 particularly heavily vibrate immediately above an area with the cavity 6 formed. When the piezoelectric layer 1 vibrates, an alternating voltage is generated on both ends of the piezoelectric layer 1 due to the piezoelectric effect. This voltage is detected by the receiver circuitry 11, and the mechanical displacement is converted to an electric signal.

Referring back to FIG. 1, the device body 10 is a device that generates ultrasound wave image data based on a reflected wave signal received by the ultrasonic probe 101. As illustrated in FIG. 1, the device body 10 includes the transmitter circuitry 9, the receiver circuitry 11, A/D converter circuitry 102, quadrature detection circuitry 103, memory 132, and processing circuitry 150. The processing circuitry 150 includes a B mode processing function 151, a Doppler processing function 152, a control function 153, and an image generating function 154.

The transmitter circuitry 9 has a rate pulse generator, transmission delay circuitry, and a transmission pulser and supplies a driving signal to the ultrasonic probe 101. The rate pulse generator repeatedly generates a rate pulse for forming a transmission ultrasound wave at a certain rate frequency. The rate pulse having a different transmission delay time by passing the transmission delay circuitry applies a voltage to the transmission pulser. The transmission delay circuitry focuses ultrasound waves generated from the ultrasonic probe 101 in a beam and adds a transmission delay time, which is allocated for each piezoelectric transducer element and is necessary for determining transmission directivity, to the rate pulse generated by the rate pulse generator. The ultrasound waves focused in a beam is referred to as an "ultrasound beam".

The transmission pulser applies a driving signal (a driving pulse) to the ultrasonic probe 101 at a timing based on the rate pulse. The driving pulse is transmitted from the transmission pulser to the ultrasonic transducer 100 in the ultrasonic probe 101 through a cable and is converted from an electric signal to mechanical vibration by the ultrasonic transducer 100. This mechanical vibration is transmitted as ultrasound waves inside the live body. The ultrasound waves having different transmission delay times for respective ultrasonic transducers 100 focus and propagate in a certain direction. The transmission delay circuitry arbitrarily adjusts a transmission direction from a vibration surface of the ultrasonic transducer 100 by changing the transmission delay time added to each rate pulse.

The transmitter circuitry 9 adds transmission directivity by controlling a transmission aperture (the number and the positions of piezoelectric transducer elements used in transmission of an ultrasound beam) using the control function 153 of the processing circuitry 150. The transmitter circuitry 9 moves the transmission aperture on every completion of transmission of ultrasound waves on a single scanning line. The transmitter circuitry 9 focuses the ultrasound waves in a beam by controlling a timing when each piezoelectric transducer element of the transmission aperture drives using the transmission delay circuitry.

The transmitter circuitry 9 has a function capable of instantly changing a transmission frequency, a transmission driving voltage, and so on so as to execute a certain scanning sequence based on an instruction from the later-described control circuitry 153. Particularly, a change in the transmission driving voltage is implemented by a linear-amplifier type transmitter circuitry capable of instantly switching the values or by a mechanism that electrically switches a plurality of power supply units.

The receiver circuitry 11 receives a reflected wave signal from the ultrasonic probe 101. More specifically, when a reflected wave of an ultrasound wave transmitted from the ultrasonic probe 101 reaches the ultrasonic transducer 100 inside the ultrasonic probe 101, the reflected wave is converted from mechanical vibration to an electric signal (a reflected wave signal) by the ultrasonic transducer 100 and is input to the receiver circuitry 11. The receiver circuitry 11 has a preamplifier and reception delay addition circuitry and generates reflected wave data as analog data by executing various kinds of processing on the reflected wave signal received by the ultrasonic probe 101.

The preamplifier performs gain adjustment by amplifying the reflected wave signal for each channel. The receiver delay addition circuitry adds a reception delay time necessary for determination of receiving directivity to the reflected wave signal. The reception delay addition circuitry further generates reflected wave data by performing addition processing (delay and addition processing) on the reflected wave signals the time phases of which become the same with the reception delay time being given. The delay and addition processing performed by the reception delay addition circuitry emphasizes reflection components from a direction corresponding to the reception directivity of the reflected wave signal.

The receiver circuitry 11 gives reception directivity by controlling a reception aperture (the number and the positions of piezoelectric transducer elements used when receiving a reflected wave signal) using the control function 153. The receiver circuitry 11 moves the reception aperture as the transmission aperture is moved. The receiver circuitry 11 generates reflected wave data for a scanning line by performing the delay and addition processing on the reflected wave signal received by each piezoelectric transducer element of the reception aperture.

In this manner, the transmitter circuitry 9 and the receiver circuitry 11 control transmission directivity and reception directivity in transmission and reception of ultrasound waves.

The A/D converter circuitry 102 digitally converts a collection signal train received by the receiver circuitry 11. The quadrature detection circuitry 103 converts reflected wave data received by the receiver circuitry 11 into an in-phase signal (I signal) and a quadrature-phase signal (Q signal) in the baseband. For example, an I signal is a signal corresponding to a cosine part (real part) of a wave subjected to the Doppler shift, whereas a Q signal is a signal corresponding to a sin part (imaginary part) of the wave subjected to the Doppler shift.

With the Doppler processing function 152, the processing circuitry 150 performs frequency analysis on reflected wave data converted into digital data by the A/D converter circuitry 102 and the quadrature detection circuitry 103 and generates data (Doppler data) in which kinetic information of a moving body (for example, a blood flow, tissues, and a contrast echo component) based on the Doppler effect is extracted. More specifically, the Doppler processing function 152 generates Doppler data in which an average velocity, a variance value, a power value, and so on are extracted over a plurality of points as kinetic information of the moving body.

When a Doppler mode is selected, a plurality of pieces of reflected wave data are collected by transmitting ultrasound waves a plurality of times on a single scanning line. The quadrature detection circuitry 103 therefore generates a plurality of IQ signals at the sample points on the single scanning line.

In the Doppler mode, a train of a plurality of IQ signals in which reflected wave data from an identical depth in data radiated a plurality of times in a single direction is arranged in time series is referred to as a "packet". The processing circuitry 150 generates a packet based on reflected wave data received by the receiver circuitry 11 using the Doppler processing function 152.

The B mode processing function 151 generates data (B mode data) representing signal intensity (amplitude intensity) with brightness by performing logarithmic amplification, envelope detection processing, logarithmic compression, and the like on the reflected wave data converted to digital data by the A/D converter circuitry 102 and the quadrature detection circuitry 103. The B mode processing function 151 can change a frequency bandwidth to be visualized by changing a detected frequency.

In the embodiment, processing functions performed by the B mode processing function 151, the Doppler processing function 152, the control function 153, and the image generating function 154 are stored in the memory 132 as computer programs executable by a computer. Processing circuitry 150 is a processor that implements a function corresponding to each computer program by reading out the computer program from the memory 132 and executing the computer program. In other words, the processing circuitry 150 having read the computer programs has functions indicated in the processing circuit 150 of FIG. 1. In FIG. 1, the functions executed by the B mode processing function 151, the Doppler processing function 152, the control function 153, and the image generating function 154 are implemented by single processing circuitry 150. Instead of this configuration, the processing circuitry 150 may be configured as a combination of a plurality of independent processors in which each of the processors executes the corresponding computer program to implement the respective functions.

In other words, the above-described functions may be configured as computer programs and processing circuitry may execute the computer programs. In another case, a certain function may be implemented in a dedicated independent program execution circuit.

The term "processor" used in the above description represents a circuit such as a central processing unit (CPU), a graphical processing unit (GPU), an application specific integrated circuit (ASIC), a programmable logic device (for example, a simple programmable logic device (SPLD)), a complex programmable logic device, and a field programmable gate array (FPGA). The processor implements functions by reading out computer programs stored in the memory 132 and executing the computer programs.

Instead of storing computer programs in the memory 132, the computer programs may be directly embedded in a circuit of the processor. In this case, the processor implements functions by reading out computer programs embedded in the circuit and executing the computer programs.

The processing circuitry 150 integrally controls the processing of the ultrasonic diagnostic device using the control function 153. Specifically, using the control function 153, the processing circuitry 150 controls processing of the transmitter circuitry 9, the receiver circuitry 11, the B mode processing function 151, the Doppler processing function 152, and the image generating function 154 based on various setting requests input from an operator through the input interface 134 and various kinds of control programs and various kinds of data read from the memory 132.

Furthermore, the processing circuitry 150 causes the control function 153 to perform control so that the display 135 can display ultrasound image data to be displayed stored in the memory 132. Examples of the memory 132 may include a semiconductor memory element such as a random access memory (RAM) and a memory device such as a hard disk and an optical disc. Examples of the B mode processing function 151, the quadrature detection circuitry 103, and the processing circuitry 150 may include an electronic circuit such as a central processing unit (CPU) and a micro processing unit (MPU) and an integrated circuit such as an application specific integrated circuit (ASIC) and a field programmable gate array (FPGA).

The processing circuitry 150 causes the image generating function 154 to generate ultrasound image data from data generated by the B mode processing function 151 and the Doppler processing function 152. The image generating function 154 of the processing circuitry 150 generates B mode image data in which intensity of a reflected wave is represented using brightness from B mode data generated by the B mode processing function 151 of the processing circuitry 150. The image generating function 154 generates color Doppler image data as an average velocity image, a variance image, a power image, or a combination thereof constituting information of the moving body from Doppler data generated by the Doppler processing function 152 of the processing circuitry 150.

The memory 132 is a memory storing image data generated by the image generating function 154 of the processing circuitry 150. The memory 132 is capable of storing data generated by the B mode processing function 151 and the Doppler processing function 152 of the processing circuitry 150.

The input interface 134 has a mouse, a keyboard, a button, a panel switch, a touchscreen, a foot switch, a trackball, a joystick, and the like. The input interface 134 receives various kinds of setting requests from an operator of the ultrasonic diagnostic device and forwards the received setting requests to the device body 10.

The display 135 displays a graphical user interface (GUI) with which the operator of the ultrasonic diagnostic device inputs various kinds of setting requests using the input interface 134, ultrasound image data generated by the device body 10, and so on.

A background according to the embodiment will now be described with reference to FIG. 3 to FIGS. 5A and 5B.

A piezoelectric micromachined ultrasound transducer (pMUT) is one of ultrasonic transducers of an ultrasonic diagnostic device. For example, the pMUT has a bimorph structure in which a monocrystalline silicon thin film and a piezoelectric thin film with electrodes disposed on both sides are laminated. Expansion and contraction of the piezoelectric thin film causes an ultrasound wave to be transmitted and received. A pMUT generally has a plurality of transducer elements aligned and driven in parallel.

Figure 3:
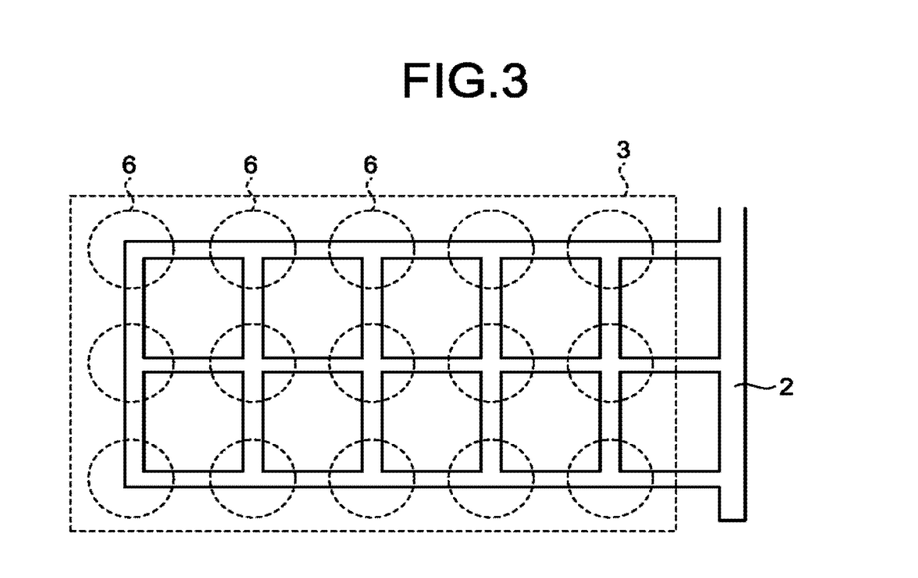
FIG. 3 is an illustrative drawing of exemplary wiring in an ultrasonic probe according to a conventional technique.
Figure 4:
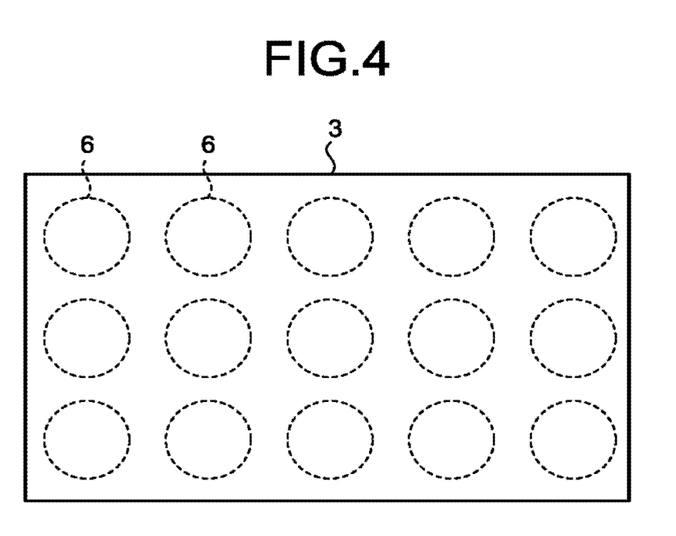
FIG. 4 is an illustrative drawing of exemplary wiring in the ultrasonic probe according to the conventional technique.

FIGS. 3 and 4 illustrate exemplary wiring of an ultrasonic probe according to a conventional technique. FIG. 3 is a drawing that illustrates wiring of the first electrode 2 (the upper electrode) according to a conventional technique. More specifically, FIG. 3 is a drawing that illustrates wiring of the first electrode 2 to a plurality of ultrasonic transducers 100 as viewed from the front side, that is, from the upper side of FIG. 2. The area surrounded by a solid line corresponds to the first electrode 2. Each cavity 6 indicated by a dotted line corresponds to a cavity 6 illustrated in FIG. 2, and the ultrasonic transducer 100 is arranged in each of the circles indicated by dotted lines in FIG. 3. FIG. 4 is a drawing that illustrates wiring of the second electrode 3 according to the conventional technique. Likewise, FIG. 4 is a drawing that illustrates wiring of the second electrode 3 (the lower electrode) to a plurality of ultrasonic transducers 100 as viewed from the front side, that is, from the upper side of FIG. 2. As seen in FIG. 4, the entire planar surface corresponds to the second electrode 3. The wiring of the second electrode 3 is indicated by a dotted line in FIG. 3 for reference. For convenience of description, in FIG. 3 and FIG. 4, the same numeral as the ultrasonic probe 101 according to the embodiment will be used.

As seen from FIG. 3 and FIG. 4, in the conventional technique, wiring of the second electrode 3 is generally arranged in a manner achieving a solid conductor pattern.

Vibration caused by an ultrasound wave transmitted and received by the ultrasonic transducer 100 is generally increased in a portion where the first electrode 2, the second electrode 3, and the cavity 6 overlap one another. An overlap portion of the first electrode 2 and the second electrode 3 is, for example, a portion where the first electrode 2 and the second electrode 3 overlap each other when viewed from the front side of the piezoelectric layer 1. Furthermore, an overlap portion of the electrode and the cavity 6 is, for example, a portion where the electrode and the cavity 6 overlap one another when viewed from the front side of the piezoelectric layer 1.

With regards to the overlap portion of the first electrode 2 and the second electrode 3 and the cavity 6 in FIG. 3, with wiring arranged in a manner of achieving a solid conductor pattern as illustrated in FIG. 3 and FIG. 4, the following exemplary two characteristics are given as characteristics of the wiring.

As a first characteristic, capacitance is generated at connection portions between the ultrasonic transducers 100, that is, for example, between the cavities 6 in FIG. 3, however, the capacitance does not contribute to transmission and reception of ultrasound waves because there is no cavity 6 in the connection portion. This construction reduces efficiency in transmission and reception ultrasound waves.

As a second characteristic, in FIG. 3, the overlap portion of the first electrode 2 and the second electrode 3 and the cavity 6 includes an edge portion (a dotted line part of the circle) of the cavity 6. The edge portion of the cavity 6 may therefore have piezoelectricity, which prevents free vibration of the transducer as a film and may degrade the frequency response. Additionally, the piezoelectricity caused at the edge portion of the cavity 6 may result in deterioration of the edge of the cavity 6.

Figure 5A:
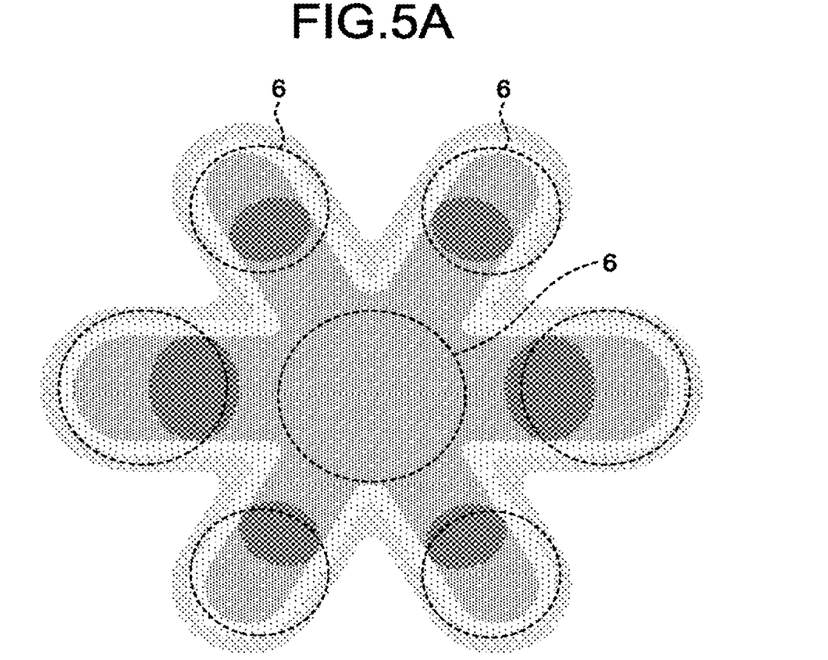
FIGS. 5A and 5B are illustrative drawings of a background according to the embodiment.
Figure 5B:
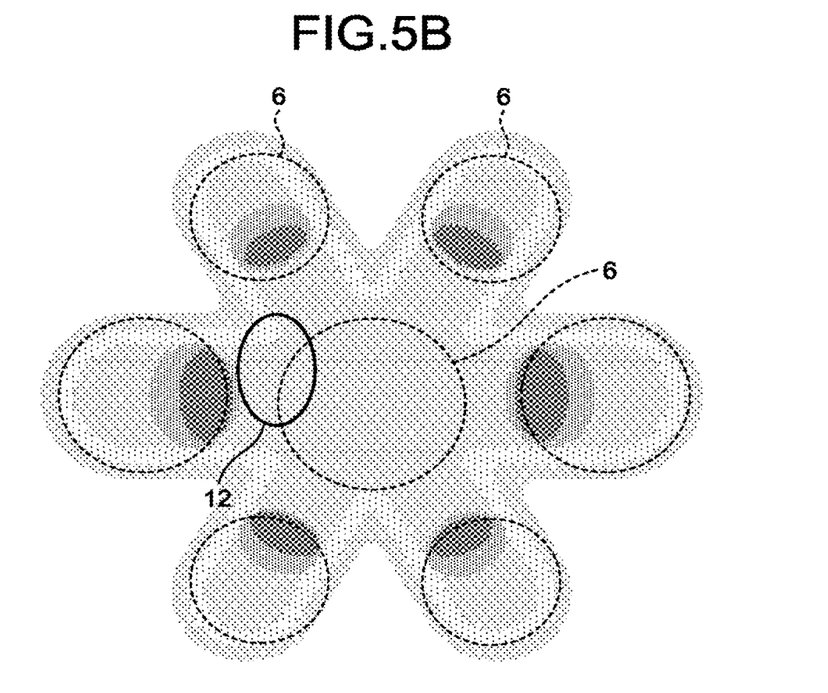

FIGS. 5A and 5B illustrate exemplary results of a simulation. In FIGS. 5A and 5B, a dotted line represents an edge of the cavity 6, and the ultrasonic transducer 100 is arranged at a position corresponding to each cavity 6. FIG. 5A illustrates potential, and specifically, a darker color represents higher potential. FIG. 5B illustrates stress applied to each portion, and specifically, a darker color represents larger stress concentration. For example, stress is concentrated at a high load area 12 illustrated in FIG. 5B, which may cause deterioration of the edge of the cavity 6.

The ultrasonic transducer 100 according to the embodiment is constructed based on the above-described background. In the embodiment, the first electrode 2 extends along a first direction. The second electrode 3 extends along a second direction intersecting with the first direction. When referring to a portion where the first electrode 2 and the second electrode 3 overlap each other when viewed from the front side of the piezoelectric layer 1 as an overlap portion, each of the first electrode 2 and the second electrode 3 has the width of the overlap portion that is larger than the width of a peripheral portion of the overlap portion. For example, the cavity 6 is formed on the back side of an overlap portion of each of the first electrode 2 and the second electrode 3 such that the overlap portion and the contour of the cavity 6 do not overlap each other.

Figure 6:
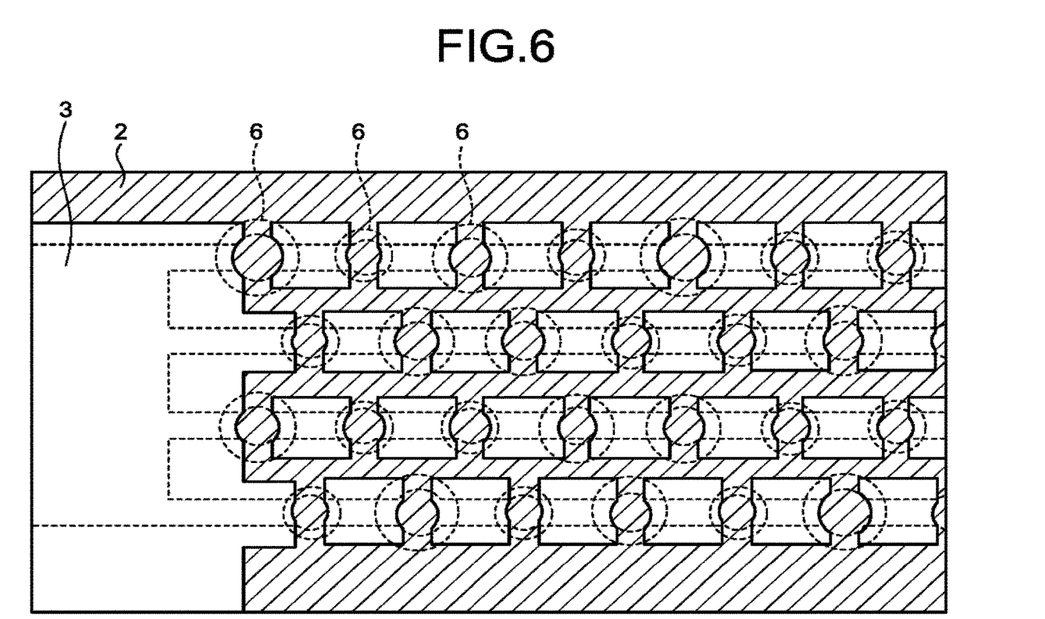
FIG. 6 and FIG. 7 are illustrative drawings of exemplary wiring in the ultrasonic probe according to the embodiment.
Figure 7:
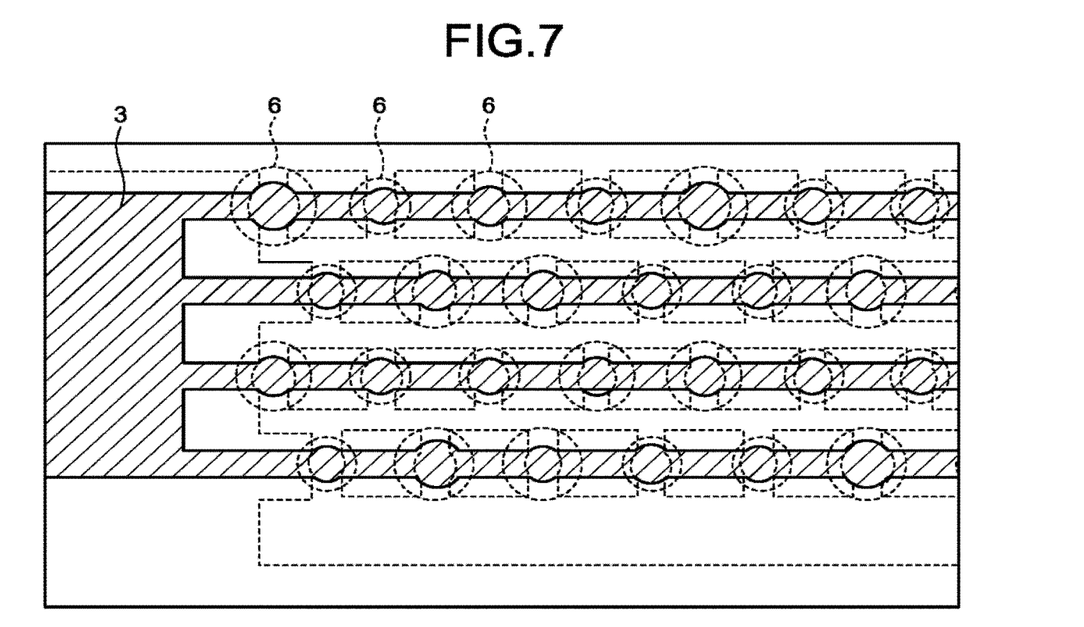

This construction will be described with reference to FIGS. 6 to 10. FIG. 6 and FIG. 7 are drawings that illustrate exemplary wiring of the ultrasonic probe 101 according to the embodiment. FIG. 6 illustrates exemplary wiring of the first electrode 2. FIG. 7 illustrates exemplary wiring of the second electrode 3. In FIG. 6 and FIG. 7, each circle indicated by a dotted line represents the cavity 6. The ultrasonic transducer 100 is arranged in each of the cavities 6. For reference, the wiring of the second electrode 3 is indicated by a dotted line in FIG. 6. Likewise, the wiring of the first electrode 2 is indicated by a dotted line in FIG. 7.

The arrangement of the ultrasonic transducers 100 will now be described. As seen from FIG. 6 and FIG. 7, the ultrasonic transducers 100 of the ultrasonic probe 101 according to the embodiment are connected in parallel by the first electrode 2 and the second electrode 3.

As illustrated in FIG. 6 and FIG. 7, the ultrasonic transducers 100 are arranged, for example, in a triangular lattice pattern to make close packing. This arrangement can increase the density of the ultrasonic transducers 100 to the maximum level while keeping the distance between the ultrasonic transducers 100. When the ultrasonic transducers 100 are arranged in a triangular lattice pattern, the wiring pattern of the first electrode 2 and the wiring pattern of the second electrode 3 intersect with each other, for example, in a stripe pattern when viewed from the front side of the piezoelectric layer 1 as illustrated in FIG. 6 and FIG. 7. In this case, the first electrode 2 extends along the first direction, that is, along the vertical direction of FIG. 6 on the periphery of the ultrasonic transducers 100. The second electrode 3 extends along the second direction intersecting with the first direction on the periphery of the ultrasonic transducers 100. The second direction is, for example, a direction intersecting with the first direction such as the horizontal direction in FIG. 7.

The ultrasonic transducers 100 may be arranged, for example, in a square lattice pattern. In this case, the wiring pattern of the first electrode 2 and the wiring pattern of the second electrode 3 intersect with each other in a mesh pattern when viewed from the front side of the piezoelectric layer 1.

With regards to the size of the cavity 6, as illustrated in FIG. 6 and FIG. 7, the cavities 6 in various different sizes are employed for an ultrasonic probe 101. Because the frequencies of transmitted and received ultrasound waves differ from one another depending on the size of the cavity 6, combination use of the ultrasonic transducers 100 having cavities 6 in respective different sizes can stabilize the frequency response of transmitted and received ultrasound waves in a wider frequency bandwidth.

Figure 8:
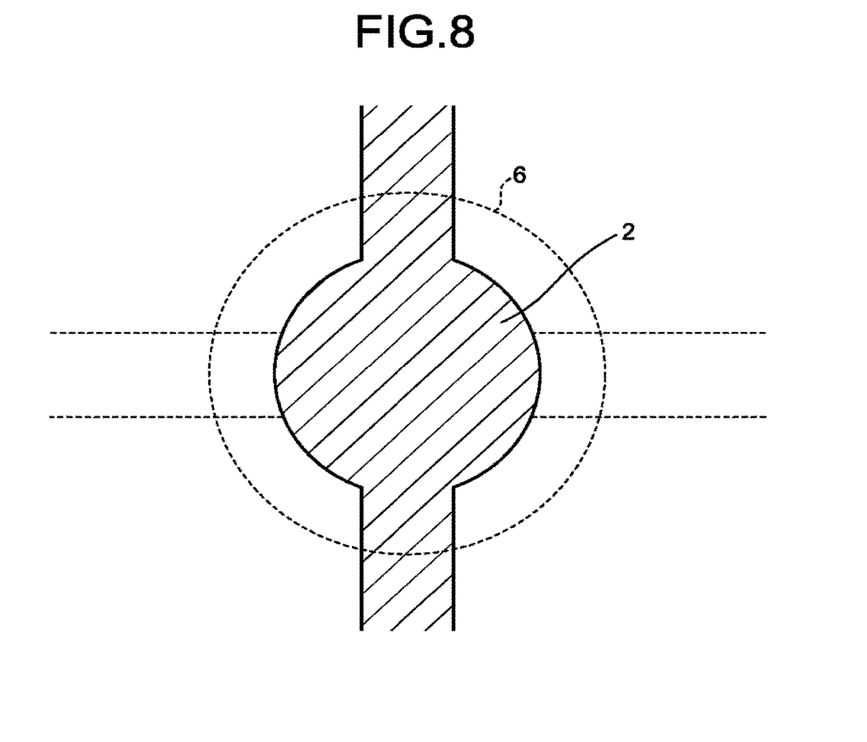
FIG. 8, FIG. 9, and FIG. 10 are more detailed illustrative drawings of wiring in the ultrasonic probe according to the embodiment.
Figure 9:
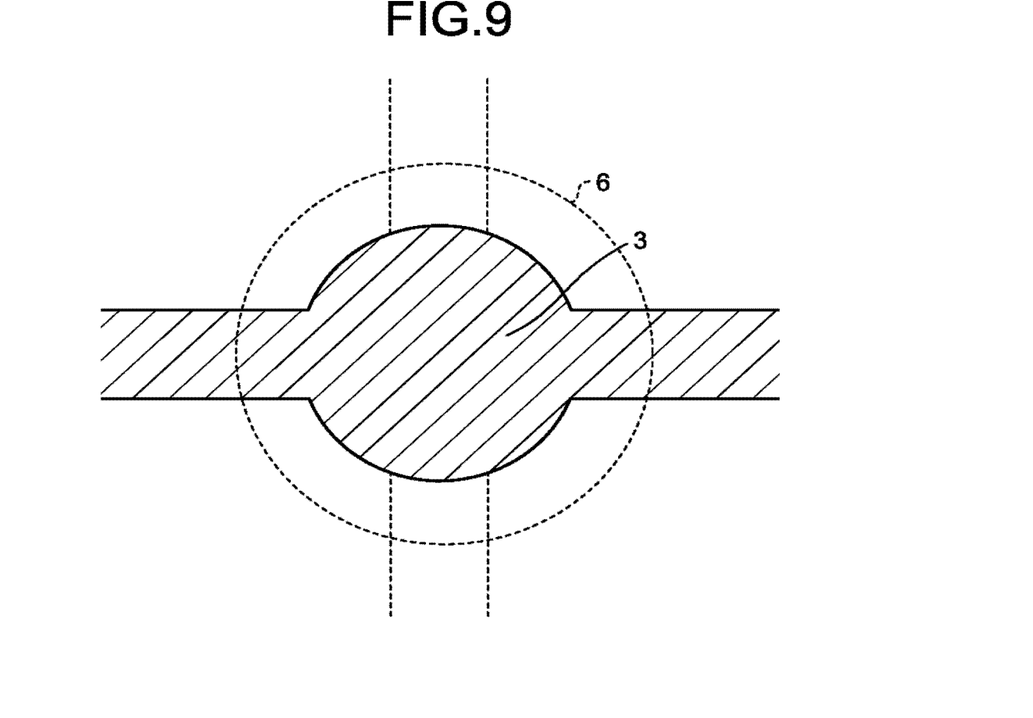
Figure 10:
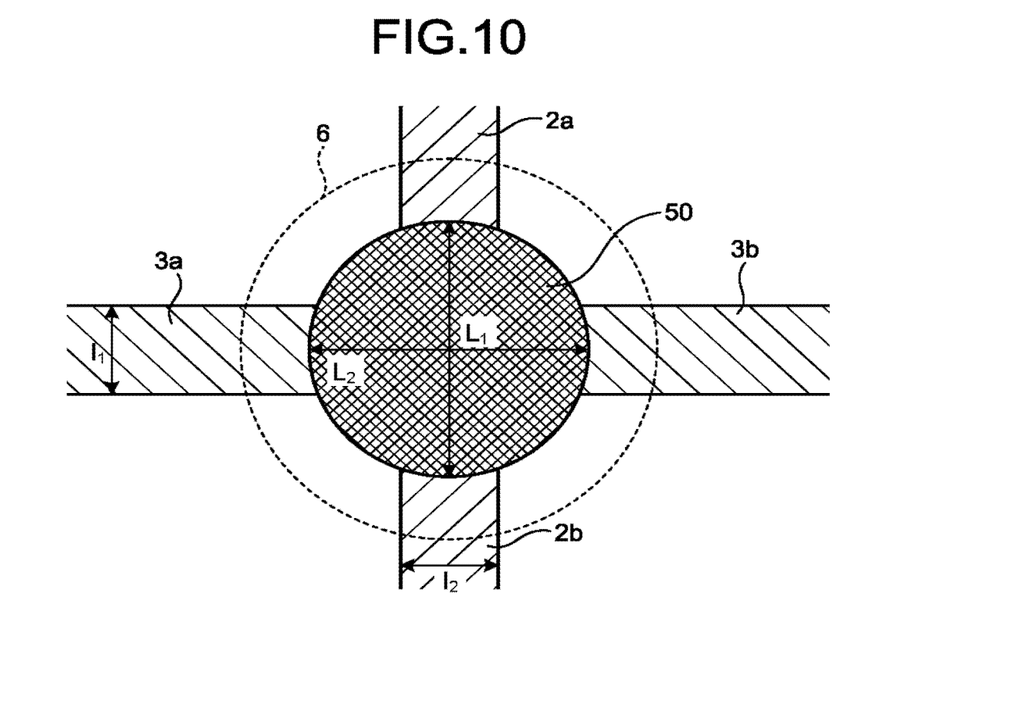

The wiring will now be described in detail with reference to FIG. 8 to FIG. 10. FIG. 8 to FIG. 10 are drawings that illustrate wiring of the ultrasonic probe 101 according to the embodiment in more details. In FIG. 8 to FIG. 10, wiring of a specific ultrasonic transducer 100 is illustrated. FIG. 8 illustrates wiring of the first electrode 2 when viewed from the front side of the piezoelectric layer 1. FIG. 9 illustrates wiring of the second electrode 3 when viewed from the front side of the piezoelectric layer 1. For reference, the wiring of the second electrode 3 is indicated by a dotted line in FIG. 8. Likewise, the wiring of the first electrode 2 is indicated by a dotted line in FIG. 9. FIG. 10 is a drawing in which FIG. 8 and FIG. 9 overlap each other.

As illustrated in FIG. 8, the first electrode 2 linearly extends along the first direction in a peripheral area distanced from an area having the ultrasonic transducer 100 and is in a circular shape in a center area having the ultrasonic transducer 100. As illustrated in FIG. 9, the second electrode 3 linearly extends along the second direction intersecting with the first direction in a peripheral area distanced from an area having the ultrasonic transducer 100 and is in a circular shape in a center area having the ultrasonic transducer 100.

FIG. 10 illustrates these structures that overlap each other. An overlap area 50 is an area of an overlap portion where the first electrode 2 and the second electrode 3 overlap each other when viewed from the front side of the piezoelectric layer 1. A peripheral area 2a and a peripheral area 2b are peripheral portions of the first electrode 2. A peripheral area 3a and a peripheral area 3b are peripheral portions of the second electrode 3. The peripheral portion includes, for example, a portion adjacent to the overlap portion while also being a pattern portion between the overlap portion and another overlap portion and a portion adjacent to the overlap portion while also being a pattern portion overlapping the cavity 6 when viewed from the front side of the piezoelectric layer 1.

In other words, as illustrated in FIG. 8, the first electrode 2 is in a circular shape in the overlap area 50 and linearly extends along the first direction in the peripheral portion of the overlap area 50. Moreover, as illustrated in FIG. 9, the second electrode 3 is in a circular shape in the overlap area 50 and linearly extends along the second direction intersecting with the first direction in the peripheral portion of the overlap area 50.

The contour shape of the overlap area 50 is formed in a manner substantially similar with the contour shape of the cavity 6. If the contour of the cavity 6 is circular, the contour of the overlap area 50 is also circularly formed. A vibration mode of the cavity 6 is determined based on the contour shape of the cavity 6. If the cavity 6 and the overlap area 50 have similar contour shapes, a pattern of external force in the piezoelectric effect and the vibration mode of the cavity 6 almost coincide with each other. With this coincidence, accuracy of transmitting and receiving ultrasound waves is less likely to be decreased.

Each of the first electrode 2 and the second electrode 3 has the width of the overlap area 50 that is larger than the width of the peripheral portion of the overlap area 50. The width of the overlap area 50 of the first electrode 2 corresponds, for example, to the length in a direction perpendicular to the longitudinal direction (the vertical direction in FIG. 10) of the first electrode 2 in the overlap area 50, that is, $L_2$. The width of the peripheral portion of the overlap area 50 in the first electrode 2 corresponds, for example, to the length in a direction perpendicular to the longitudinal direction (the vertical direction in FIG. 10) of the first electrode 2 in the peripheral area 2a and the peripheral area 2b, that is, $l_2$. The first electrode 2 therefore has the width $L_2$ of the overlap area 50 that is larger than the width $l_2$ of the peripheral portion of the overlap area 50. The width of the overlap area 50 of the second electrode 3 corresponds, for example, to the length in a direction perpendicular to the longitudinal direction (the lateral direction in FIG. 10) of the second electrode 3 in the overlap area 50, that is, $L_1$. The width of the peripheral portion of the overlap area 50 in the second electrode 3 corresponds, for example, to the length in a direction perpendicular to the longitudinal direction (the lateral direction in FIG. 10) of the second electrode 3 in the peripheral area 3a and the peripheral area 3b, that is, $l_1$. The second electrode 3 therefore has the width $L_1$ of the overlap area 50 that is larger than the width $l_1$ of the peripheral portion of the overlap area 50.

Figure 11:
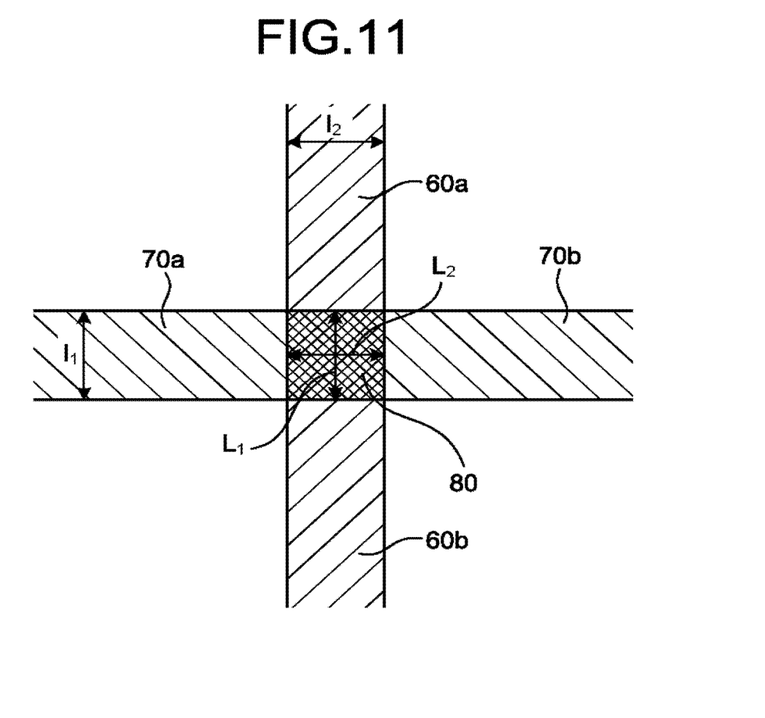
FIG. 11 is an illustrative drawing of wiring different from the wiring of FIG. 10.

FIG. 11 illustrates a construction in which the width of an overlap area 80 is not larger than the width of a peripheral portion of the overlap area 80. FIG. 11 is a drawing that illustrates wiring different from that of FIG. 10. FIG. 11 is a drawing in which the wiring of the first electrode 2 and the wiring of the second electrode 3 overlap each other as illustrated in FIG. 10. The overlap area 80 is an area of an overlap of the first electrode 2 and the second electrode 3. Peripheral areas 60a and 60b are peripheral portions of the overlap area 80 in the first electrode 2. Peripheral areas 70a and 70b are peripheral portions of the overlap area 80 in the second electrode 3. In FIG. 11, the first electrode 2 has the width $L_2$ of the overlap area 80 that is equal to the width 12 of the peripheral portion of the overlap area 80. The second electrode 3 has the width $L_1$ of the overlap area 80 that is equal to the width $l_1$ of the peripheral portion of the overlap area 80.

As seen from comparison between FIG. 10 and FIG. 11, a large width of the overlap area 50 means a large effective area of a piezoelectric film, which is an area contributing to the piezoelectric effect. The ultrasonic probe 101 according to the embodiment therefore has a large effective area on the piezoelectric film, which improves efficiency in transmitting and receiving ultrasound waves.

Each of the first electrode 2 and the second electrode 3 has the width of the overlap area 50 and the width of the peripheral portion of the overlap area 50 that are smaller than the diameter of the cavity 6. In the example of FIG. 10, the first electrode 2 has the width $L_2$ of the overlap area 50 and the width $l_2$ of the peripheral portion of the overlap area 50 that are smaller than the diameter of the cavity 6. Similarly, the second electrode 3 has the width $L_1$ of the overlap area 50 and the width $l_1$ of the peripheral portion of the overlap area 50 that are smaller than the diameter of the cavity 6.

The overlap area 50 therefore can be formed in a manner not overlapping the contour of the cavity 6. For example, with the widths $L_1$ and $L_2$ of the overlap area 50 formed to be approximately 60% as large as the diameter of the cavity 6, the overlap area 50 and the contour of the cavity 6 can be formed in a manner not overlapping each other. As described above, an overlap of the overlap area 50 and the contour of the cavity 6 causes deterioration of the edge of the cavity 6. In this point, the construction described in the embodiment is advantageous in preventing deterioration of the edge of the cavity 6.

As described above, according to the embodiment, the transmission and reception sensitivity of an ultrasonic transducer can be improved.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic transducer comprising:
a piezoelectric layer;
a first electrode that is positioned in a front side of the piezoelectric layer and extends along a first direction;
a second electrode that is positioned in a back side of the piezoelectric layer and extends along a second direction intersecting with the first direction;
a base layer that is positioned in a back side of the second electrode; and
a substrate that is positioned in a back side of the base layer, wherein
each of the first electrode and the second electrode includes an overlap portion where the first electrode and the second electrode overlap each other when viewed from the front side of the piezoelectric layer,
the substrate is provided with a cavity in a back side of the overlap portion on each of the first electrode and the second electrode, and
each of the first electrode and the second electrode has a width of the overlap portion that is larger than a width of a peripheral portion of the overlap portion, wherein
a contour of the overlap portion is circular; and
a diameter of the overlap portion is smaller than a diameter of the cavity.

2. The ultrasonic transducer according to claim 1, wherein each of the first electrode and the second electrode has the width of the overlap portion and the width of the peripheral portion of the overlap portion that are smaller than the diameter of the cavity.

3. The ultrasonic transducer according to claim 1, wherein a contour of the cavity is circular.

4. The ultrasonic transducer according to claim 1, wherein a contour of the overlap portion and a contour of the cavity are substantially in similar shapes.

5. The ultrasonic transducer according to claim 1, wherein a contour of the overlap portion and a contour of the cavity do not overlap each other.

6. An ultrasonic probe comprising a plurality of the ultrasonic transducers according to claim 1.

7. The ultrasonic probe according to claim 6, wherein the plurality of ultrasonic transducers are connected in parallel by wiring of the first electrode and wiring of the second electrode.

8. The ultrasonic probe according to claim 7, wherein a wiring pattern of the first electrode and a wiring pattern of the second electrode intersect with each other in a mesh pattern or in a stripe pattern when viewed from the front side of the piezoelectric layer.

9. The ultrasonic probe according to claim 7, wherein the plurality of ultrasonic transducers are arranged in a triangular lattice pattern.

10. An ultrasonic transducer comprising:
a piezoelectric layer;
a first electrode disposed on a front side of the piezoelectric layer and extending along a first direction;
a second electrode disposed on a back side of the piezoelectric layer and extending along a second direction intersecting with the first direction;
a base layer disposed on a back side of the second electrode; and
a substrate disposed under a back side of the base layer, wherein
each of the first electrode and the second electrode includes a circular overlap portion where the first electrode and the second electrode overlap each other when viewed from the front side of the piezoelectric layer, and the substrate is provided with a cavity corresponding in position to the overlap portions of the first electrode and the second electrode when viewed from the front side of the piezoelectric layer, wherein the cavity is circular, and a diameter of the cavity is larger than diameters of each of the overlap portions of the first and second electrodes.

11. The ultrasonic probe according to claim 10, wherein diameters of the overlap portions of the first and second electrodes are each about 60% of a diameter of the cavity.

12. The ultrasonic probe according to claim 10, wherein the overlap portions of each of the first electrode and the second electrodes are disposed within a periphery of the cavity when viewed from the front side of the piezoelectric layer.

13. An ultrasonic transducer comprising:

a piezoelectric layer;

a first electrode that is disposed on a front side of the piezoelectric layer, extends along a first direction, and has a portion with an outer periphery having a substantially circular shape with a first diameter;

a second electrode that is disposed on a back side of the piezoelectric layer and extends along a second direction intersecting with the first direction;

a base layer that is disposed on a back side of the second electrode; and a substrate that is disposed on a back side of the base layer, wherein the substrate comprises a cavity having a circular shape with a second diameter positioned to be located within the outer periphery of the portion of the first electrode when viewed from the front side of the piezoelectric layer, and the second diameter is smaller than the first diameter.

14. The ultrasonic transducer according to claim 10, wherein:

the first electrode has first and second linear sections extending from opposing edges of the overlap portion of the first electrode;

the first and second linear sections each extend longitudinally in the first direction and do not overlap with the second electrode when viewed from the front side of the piezoelectric layer;

the second electrode has third and fourth linear sections extending from opposing edges of the overlap portion of the second electrode; and the third and fourth linear sections each extend longitudinally in the second direction and do not overlap with the first electrode when viewed from the front side of the piezoelectric layer.

15. The ultrasonic transducer according to claim 14, wherein the first direction is substantially perpendicular to the second direction.

16. The ultrasonic transducer according to claim 14, wherein:

a width of each of the first and second linear sections is less than a width of the overlap portion of the first electrode; and a width of each of the third and fourth linear sections is less than a width of the overlap portion of the second electrode.

* * * * *